United States Patent
Havel et al.

(10) Patent No.: US 7,181,273 B2
(45) Date of Patent: Feb. 20, 2007

(54) TACHYCARDIA SYNCHRONIZATION DELAYS

(75) Inventors: William J. Havel, Maple Grove, MN (US); Paul J. Degroot, Brooklyn Park, MN (US); Paul M. Stein, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 585 days.

(21) Appl. No.: 10/418,853

(22) Filed: Apr. 18, 2003

(65) Prior Publication Data

US 2004/0210257 A1 Oct. 21, 2004

(51) Int. Cl.
*A61N 1/39* (2006.01)

(52) U.S. Cl. .................. 607/5; 607/4; 607/7

(58) Field of Classification Search ............. 607/4–5, 607/7
See application file for complete search history.

(56) References Cited

U.S. PATENT DOCUMENTS

| | | | |
|---|---|---|---|
| 3,805,795 A | 4/1974 | Denniston et al. .......... 128/419 |
| 3,952,750 A | 4/1976 | Mirowski et al. | |
| 4,114,628 A | 9/1978 | Rizk .................... 128/419 |
| 4,316,472 A | 2/1982 | Mirowski et al. | |
| 4,384,585 A * | 5/1983 | Zipes ................... 607/5 |
| 4,407,288 A | 10/1983 | Langer et al. | |
| 4,572,191 A | 2/1986 | Mirowski et al. | |
| 4,830,006 A | 5/1989 | Haluska et al. | |
| 5,188,105 A | 2/1993 | Keimel .................. 128/419 |
| 5,193,536 A | 3/1993 | Mehra .................... 128/419 |
| 5,275,621 A | 1/1994 | Mehra | |
| 5,578,062 A | 11/1996 | Alt et al. | |
| 5,601,609 A | 2/1997 | Duncan | |
| 5,851,220 A * | 12/1998 | Murphy .................. 607/5 |
| 5,954,752 A | 9/1999 | Mongeon et al. | |
| 2004/0167579 A1 * | 8/2004 | Sharma et al. .......... 607/14 |

FOREIGN PATENT DOCUMENTS

EP 0 815 900 A2 6/1997

* cited by examiner

*Primary Examiner*—Robert Pezzuto
*Assistant Examiner*—Shevon Johnson
(74) *Attorney, Agent, or Firm*—Girma Wolde-Michael; Paul H. McDowall

(57) ABSTRACT

An implantable medical device (IMD) provides for adaptive timing of the delivery of cardioversion shocks. In particular, the invention IMD provides for an adaptive cardioversion synchronization delay with respect to a cardiac event, such as a sensed P-wave or R-wave. When cardioversion with a first synchronization delay fails to terminate a tachycardia, for example, cardioversion may be attempted again with a second synchronization delay. The IMD may keep track of whether each synchronization delay is effective in terminating the tachycardia, and may employ a historically effective synchronization delay when applying cardioversion therapy to treat a subsequent tachycardia episode.

24 Claims, 4 Drawing Sheets

TACHYCARDIA SYNCHRONIZATION DELAYS

TECHNICAL FIELD

The invention relates to implantable medical devices, and more particularly, to implantable medical devices that treat tachycardia.

BACKGROUND

Tachycardia is an abnormal heart rhythm characterized by rapid activation of one or more chambers of the heart of a patient. Tachycardia is often qualified by the locus of origin: a tachycardia that originates in the ventricles of the heart is called a ventricular tachycardia (VT) and a tachycardia that originates in the atria of the heart is called an atrial tachycardia (AT) or a supraventricular tachycardia (SVT). Some VTs, if untreated, may accelerate into ventricular fibrillation (VF), in which the pumping ability of the heart is seriously impaired.

There are many therapies that may be applied to treat tachycardia. Some tachycardias respond well to medication, and others may be treated with surgery such as radio frequency (RF) ablation. In some patients, VT or AT may respond well to antitachycardia pacing (ATP), in which small electric stimulations from an implantable pulse generator (IPG) in an implantable medical device (IMD) disrupt the propagation of electrical signals that cause the tachycardia.

In some circumstances, however, a tachycardia may fail to terminate in response to therapies such as these. Some IMDs may therefore include the capability of delivering a higher energy cardioversion shock to terminate the tachycardia. Cardioversion is an effective therapy in treating well organized single loop tachycardias. Application of a cardioversion shock at a particular moment depolarizes cardiac tissue to prevent re-entry, thereby terminating the tachycardia.

In conventional cardioversion therapy, an IMD delivers a cardioversion shock synchronized to a cardiac event, such as an R-wave that accompanies a ventricular depolarization. In other words, the IMD delivers the cardioversion shock at a fixed time in relation to the event. The IMD may, for example, time the delivery of a cardioversion shock promptly upon detection of an R-wave.

An external device, such as an external defibrillator, likewise may be capable of applying cardioversion therapy. Like implanted devices, external devices may sense cardiac events and may apply cardioversion shocks synchronized to the cardiac events.

SUMMARY

In general, the invention provides for adaptive timing of the delivery of cardioversion shocks. In particular, the invention provides for an adaptive cardioversion synchronization delay with respect to a cardiac event, such as a sensed P-wave or R-wave. When cardioversion with a first synchronization delay fails to terminate a tachycardia, cardioversion is attempted again with a second synchronization delay. A medical device may keep track of whether each synchronization delay is effective in terminating the tachycardia.

If a synchronization delay is effective, it is more likely to be employed again to terminate a subsequent tachycardia episode. A processor in a medical device may select a synchronization delay as a function of historical effectiveness.

In one embodiment, the invention is directed to a method comprising applying a first cardioversion shock to a heart experiencing a tachycardia. The first cardioversion shock is applied with a first synchronization delay with respect to a first cardiac event. The method also includes monitoring whether the first cardioversion shock terminates the tachycardia, and applying a second cardioversion shock to the heart when the first cardioversion shock fails to terminate the tachycardia. The second cardioversion shock is applied with a second synchronization delay with respect to a second cardiac event. A third cardioversion shock with a third synchronization delay may be applied if the second cardioversion shock fails to terminate the tachycardia. When treating subsequent episodes of tachycardia, the method may provide that a synchronization delay may be selected that was historically effective in treating previous episodes.

In other embodiments, the invention may be directed to a computer-readable medium comprising instructions for causing a programmable processor to carry out the techniques described above.

In a further embodiment, the invention presents a medical device comprising sensing circuitry to sense a first cardiac event and a second cardiac event in a heart experiencing a tachycardia, and cardioversion circuitry to apply a first cardioversion shock and a second cardioversion shock to the heart. The device further includes control circuitry to apply the first cardioversion shock with a first synchronization delay with respect to the first cardiac event, and to apply the second cardioversion shock with a second synchronization delay with respect to a second cardiac event when the first cardioversion shock fails to terminate the tachycardia. The device may further include one or more sense electrodes to sense the cardiac events, and one or more cardioversion electrodes to apply the cardioversion shocks. The device may further include a processor to select synchronization delays.

The details of one or more embodiments of the invention are set forth in the accompanying drawings and the description below. Other features and inventive aspects of the invention will be apparent from the description and drawings, and from the claims.

DETAILED DESCRIPTION

Figure 1:
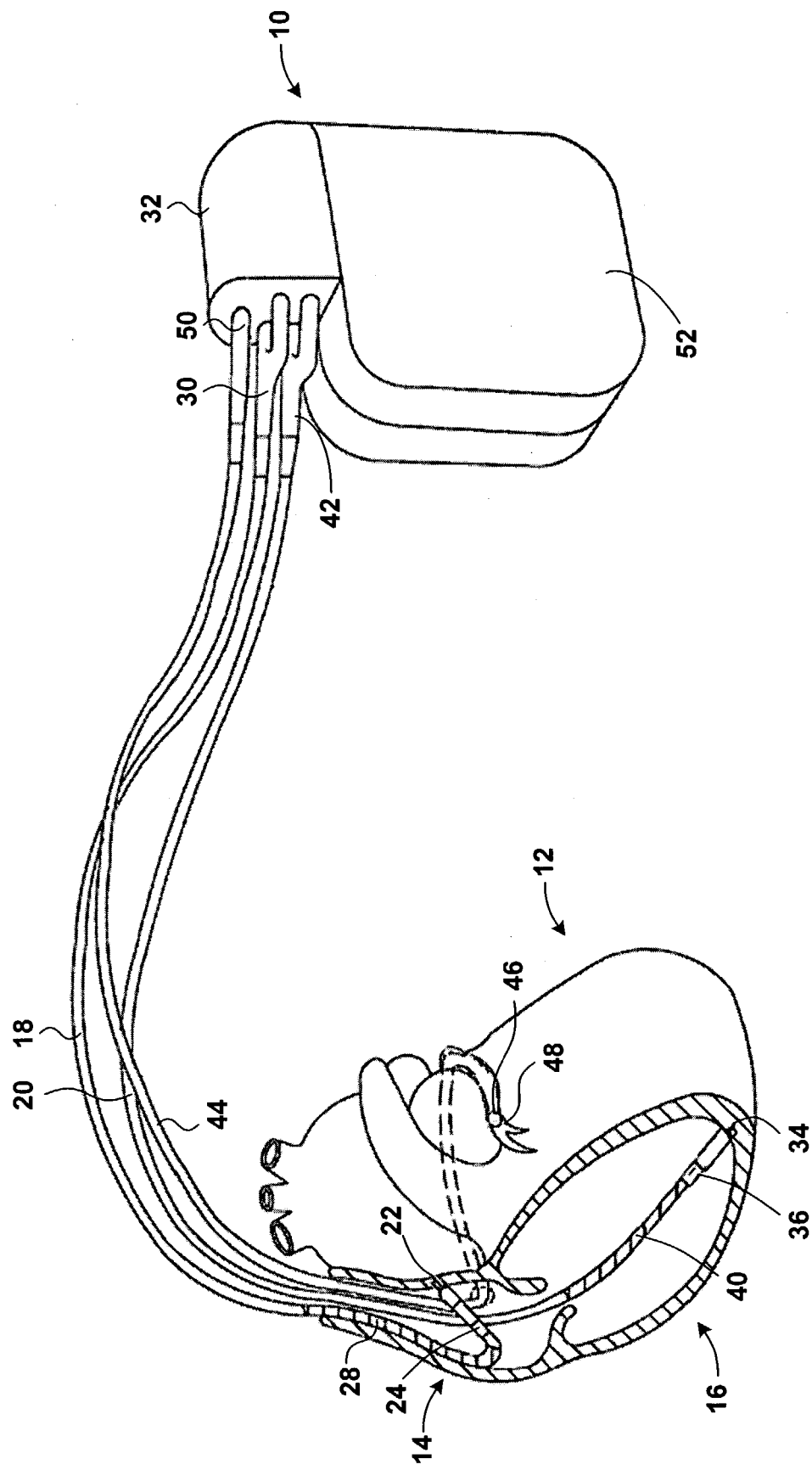
FIG. 1 is a schematic illustration of an atrial and ventricular chamber pacemaker/cardioverter/defibrillator with leads extending to a human heart.

FIG. 1 depicts an exemplary implantable medical device (IMD) 10 that may practice the techniques of the invention. IMD 10 is configured to apply cardioversion shocks to heart 12, and to time delivery of the cardioversion shocks adaptively. In particular, IMD 10 applies cardioversion shocks with a synchronization delay with respect to a cardiac event, such as a detected P-wave or R-wave, and may apply the shocks to treat atrial tachycardia (AT) or ventricular tachycardia (VT), or both.

In the example of FIG. 1, IMD 10 is an implantable multi-chamber pacemaker/cardioverter/defibrillator that includes anti-tachycardia pacing (ATP), cardioversion and defibrillation capabilities. The invention is not limited to the particular IMD shown in FIG. 1, however, but may be practiced by any number of implantable devices. The techniques of the invention may be practiced by a device that paces and/or shocks a single cardiac chamber or several chambers, that paces and/or shocks one or more atria or one or more ventricles, and that paces in any of several pacing modes. Although it is advantageous if the implantable device is capable of applying ATP, ATP capability is not necessary to the invention.

Although the invention will be described in the context of an IMD, the techniques are not limited to application in implantable medical devices. An external medical device such as an external defibrillator may include the capabilities of detecting tachycardia and applying one or more cardioversion shocks to terminate the tachycardia. The external device may detect cardiac events such as atrial and ventricular activations, and may apply cardioversion shocks with a synchronization delays with respect to a cardiac event.

IMD 10 includes an implantable pulse generator (IPG) (not shown in FIG. 1) that generates pacing stimuli to administer one or more pacing therapies to heart 12. Pacing therapies may include ATP therapies or antibradycardia pacing, for example. In the embodiment shown in FIG. 1, pacing stimuli may be applied to the right atrium 14 or the right ventricle 16, or both. IMD 10 also includes circuitry to sense atrial and ventricular activations, including activations that may be generated during episodes of AT or VT. Atrial and ventricular bipolar pace/sense electrode pairs at the distal ends of leads 18 and 20, respectively, carry out the pacing and sensing functions.

In right atrium 14, the distal end of atrial lead 18 includes a pace/sense tip electrode 22 and a pace/sense ring electrode 24. Pace/sense electrodes 22 and 24 are employed for atrial pacing, including delivery of atrial ATP therapies, and for sensing of P-waves indicative of atrial activation. The distal end of atrial lead 18 also includes an elongated coil defibrillation electrode 28 that can deliver a cardioversion shock or defibrillation shock to right atrium 14.

Atrial lead 18 may include conductors that electrically couple electrodes 22, 24 and 28 to IMD 10. The conductors may be arranged coaxially, coradially, in parallel, or in another configuration, and may be insulated from one another and from the tissue of the patient. The proximal end of atrial lead 18 may include a bifurcated connector 30 that couples the conductors to a connector block 32 on IMD 10.

In right ventricle 16, the distal end of ventricular lead 20 likewise may include a pace/sense tip electrode 34 and a pace/sense ring electrode 36. Pace/sense tip electrode 34 is deployed in the apex of heart 12. Pace/sense electrodes 34 and 36 are employed for ventricular pacing, including delivery of ventricular ATP therapies, and for sensing of R-waves indicative of ventricular activation. The distal end of ventricular lead 20 also includes an elongated coil defibrillation electrode 40 that can deliver a cardioversion shock or defibrillation shock to right ventricle 16. Cardioversion therapy, which is applied to treat VT, typically involves delivery of less energy to heart 12 than defibrillation therapy, which is applied to treat VF.

Like atrial lead 18, ventricular lead 20 may include one or more insulated conductors that electrically couple electrodes 34, 36 and 40 to IMD 10. The proximal end of ventricular lead 20 may include a bifurcated connector 42 that couples the conductors to connector block 32.

FIG. 1 illustrates deployment of a coronary sinus lead 44. Coronary sinus lead 44 may include one or more insulated conductors. The proximal end of coronary sinus lead 44 may include one or more electrodes, such as pace/sense electrode 46. Pace/sense electrode 46 may be deployed within the great vein 48 of heart 12, and may be used to deliver pacing therapies, including ATP therapies, to the left side of heart 12. A connector 50 at the proximal end of the coronary sinus lead 44 couples the conductors in lead 44 to connector block 32. In some embodiments of the invention, coronary sinus lead 44 may include an elongated exposed coil wire defibrillation electrode (not shown) that is capable of applying cardioversion or defibrillation therapies.

IMD 10 includes a housing 52 that, in some embodiments of the invention, serves as a "can" electrode. In unipolar operation, IMD 10 may deliver an electrical stimulation to heart 12 via an electrode disposed on one or more of leads 18, 20 or 44, with housing 52 being a part of the return current path. In bipolar operation, by contrast, IMD 10 may deliver an electrical stimulation to heart 12 via a tip electrode, with a ring electrode providing the principal return current path.

In the embodiment depicted in FIG. 1, IMD 10 delivers pacing stimuli to right atrium 14 and right ventricle 16 via electrodes 22 and 34, respectively, and senses activations via the same electrodes. The electrodes sense the electrical activity that accompanies AT or VT. The electrodes also deliver one or more ATP therapies to treat AT or VT. The energy for pacing pulses generated by the IPG, as well as the energy for cardioversion and defibrillation shocks, comes from a power supply such as a battery (not shown) inside housing 52.

The invention provides techniques for adaptive timing of the delivery of cardioversion shocks. In particular, the invention provides for an adaptive cardioversion synchronization delay with respect to a cardiac event, such as a detected P-wave or R-wave. The techniques of the invention may be applied to treat AT via elongated atrial coil electrode 28, or to treat VT via elongated ventricular coil electrode 40, or both.

With these techniques, IMD 10 may apply a cardioversion therapy that is more likely to treat an atrial or ventricular tachycardia effectively and efficiently. The treatment is more likely to be effective because the treatment is more likely to terminate the tachycardia. The treatment is more likely to be efficient because less energy can be used to terminate the tachycardia. In many forms of tachycardia, timing of the cardioversion therapy is important to success, and a cardioversion therapy applied with one synchronization delay may be as effective or more effective at a lower energy level than a cardioversion therapy applied with a different synchronization delay at a higher energy level. As a result, the effective timing of cardioversion therapy may allow termination of tachycardias with lower energy levels, thereby conserving battery power of IMD 10. Techniques for application of cardioversion therapy with an adaptive synchronization delay will be described in more detail below.

Figure 2:
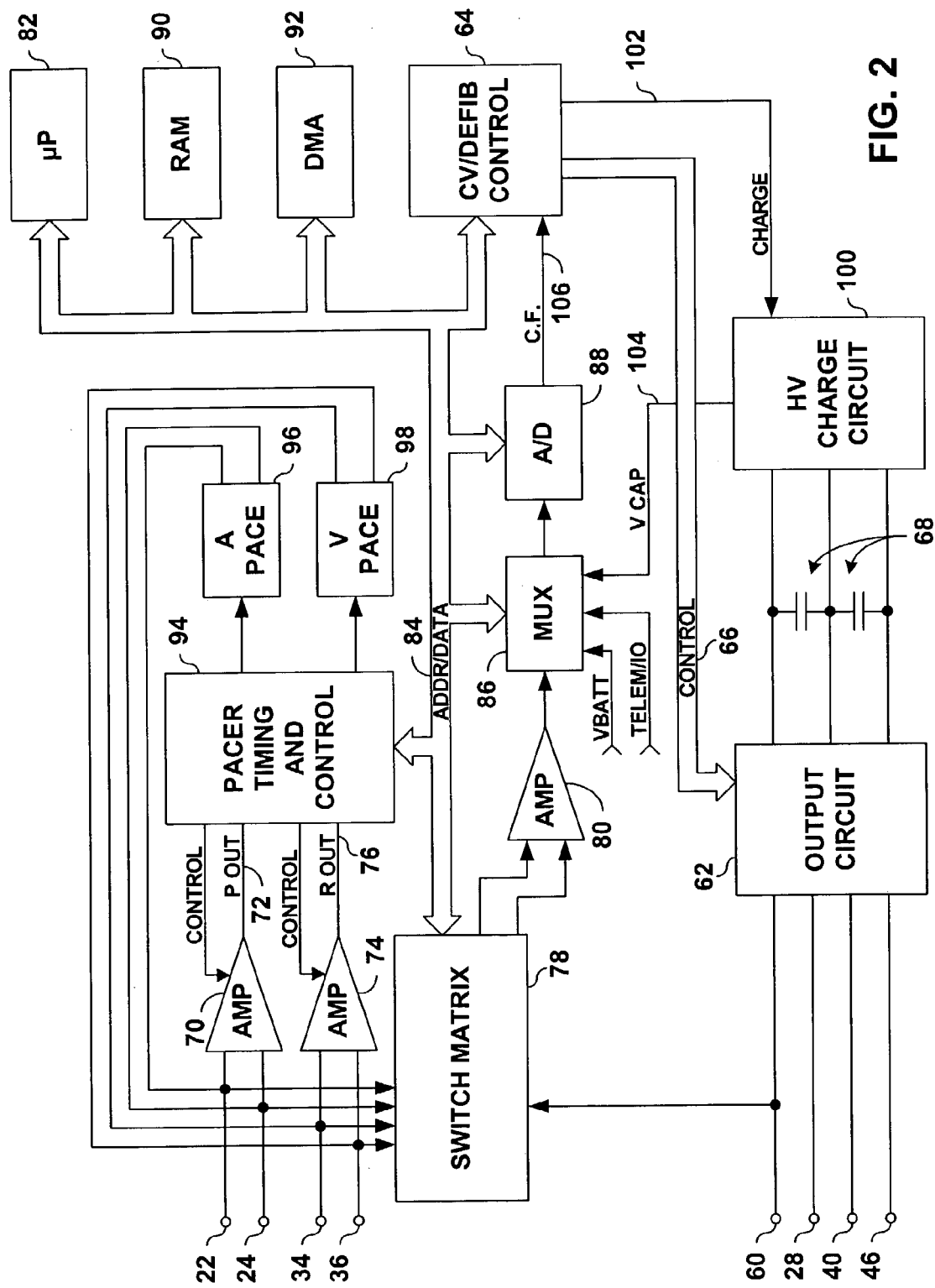
FIG. 2 is a block diagram of the implantable medical device depicted in FIG. 1.

FIG. 2 is a functional schematic diagram of one embodiment of IMD 10 and illustrates how IMD 10 detects episodes of tachycardia and delivers therapies, such as ATP and cardioversion, to address the episodes. This diagram is exemplary of the type of device in which various embodiments of the invention may be embodied, and the invention is not limited to the particular schematic shown. On the contrary, the invention may be practiced in a wide variety of devices, including single- and multi-chamber devices, and implantable devices that do not include ATP capability.

FIG. 2 includes electrode terminals 22, 24, 28, 34, 36, 40 and 46, which correspond to the electrodes shown in FIG. 1. Electrode 60 corresponds to the uninsulated portion of housing 52 of IMD 10. Electrodes 28, 40 and 46 are coupled to high voltage output circuit 62, which includes high voltage switches controlled by cardioversion/defibrillation (CV/defib) control logic 64 via control bus 66. Switches disposed within circuit 62 determine which electrodes are employed and which electrodes are coupled to the positive and negative terminals of a capacitor bank 68 during delivery of defibrillation or cardioversion shocks.

Electrodes 22 and 24, located on or in right atrium 14, are coupled to a P-wave amplifier 70. Amplifier 70 may comprise an automatic gain controlled amplifier providing an adjustable sensing threshold as a function of the measured P-wave amplitude. Amplifier 70 generates a signal on P-out line 72 whenever the signal sensed between electrodes 22 and 24 exceeds the sensing threshold. The time intervals between signals on P-out line 72 reflect the cycle length of atrial activations, and may be indicative of whether the patient is experiencing an episode of AT. In particular, short cycle lengths may be indicative of AT.

Electrodes 34 and 36, located in right ventricle 16, are coupled to an R-wave amplifier 74. Amplifier 74 may comprise an automatic gain controlled amplifier providing an adjustable sensing threshold as a function of the measured R-wave amplitude. Amplifier 74 generates a signal on R-out line 76 whenever the signal sensed between electrodes 34 and 36 exceeds the sensing threshold of amplifier 74. The time intervals between signals on R-out line 76 reflect the cycle length of ventricular activations and may be indicative of whether the patient is experiencing an episode of VT.

Signals on P-out line 72 and R-out line 76 may be used to signal cardiac events. In particular, signals on P-out line 72 and R-out line 76 reflect sensed atrial and ventricular activations. As will be described below, IMD 10 uses one or more of these cardiac events to time the delivery of cardioversion shocks. Signals on P-out line 72 and R-out line 76 may further reflect whether a previously detected tachycardia has been terminated. In general, longer time intervals between signals on P-out line 72 and R-out line 76 may be indicative of a return to a normal sinus rhythm.

A switch matrix 78 may select electrodes for coupling to a wide band amplifier 80 for use in digital signal analysis. Selection of electrodes is controlled by microprocessor 82 via data/address bus 84. The signals from the selected electrodes are provided to multiplexer 86, and are thereafter converted to multi-bit digital signals by A/D converter 88. The signals may be stored in random access memory (RAM) 90 under control of direct memory access (DMA) circuit 92.

Digital signal analysis includes, but is not limited to, a morphological analysis of waveforms sensed by the selected electrodes. Morphological analysis may comprise wavelet analysis, Fourier analysis or similar spectral analysis techniques, but the invention is not limited to those analytical techniques. Microprocessor 82 may employ digital signal analysis techniques to characterize the digitized signals stored in RAM 90 to recognize and classify the patient's heart rhythm or to determine the morphology of the signals employing any of several signal processing methodologies.

Signals sensed via electrodes 22, 24, 34 and 36 may be used to determine whether to administer cardiac pacing, ATP, cardioversion or defibrillation therapies. Pacer timing/ control circuitry 94 receives signals from P-out line 72 and R-out line 76, and computes various timing intervals as a function of the timing of the received signals. Pacer timing/ control circuitry 94 also may include programmable digital counters that control pacing according to any of several pacing modes.

Pacer output circuitry 96 and 98, which are coupled to electrodes 22, 24, 34 and 36, generate pacing and ATP stimuli under the control of pacer timing/control circuitry 94. The IPG of IMD 10 comprises microprocessor 82, in cooperation with pacer timing/control circuitry 94 and pacer output circuitry 96 and 98.

Pacer timing/control circuitry 94 may also compute intervals such as R—R intervals, P—P intervals, P-R intervals and R-P intervals. These intervals may be used to detect the presence of a fast heart rate, which may be an indicator of a tachycardia or fibrillation. A fast heart rate may also be indicative of sinus tachycardia, i.e., a fast heart rate in response to a physiological stimulus, such as exercise. Microprocessor 82 and pacer timing/control circuitry 94 may cooperate to apply any of a number of algorithms to discriminate a tachycardia such as VT or AT, for which antitachycardia therapy may be indicated, from sinus tachycardia, for which therapy is not indicated. Microprocessor 82 and pacer timing/control circuitry 94 may further cooperate to apply any of a number of algorithms to discriminate a tachycardia such as VT or AT, which may terminate in response to antitachycardia therapies, from other tachyarrhythmias such as atrial fibrillation and ventricular fibrillation, which generally do not respond to antitachycardia therapies. The invention may be practiced with any algorithm or algorithms that detect an atrial or ventricular tachycardia.

When IMD 10 detects an atrial or ventricular tachycardia, microprocessor 82 may select an ATP regimen that comprises a plurality of ATP therapies arranged in a hierarchy. In general, the first ATP therapy in a hierarchy is applied initially. If the first ATP therapy fails to terminate the tachycardia, the second ATP therapy in the hierarchy is applied, and so on. For each ATP therapy that is applied, microprocessor 82 loads parameters such as timing intervals from RAM 90 into pacer timing/control circuitry 94, which controls delivery of the ATP therapy. Microprocessor 82 evaluates the outcome of the ATP therapy, and determines whether ATP therapy should be discontinued or whether the next therapy in the hierarchy ought to be applied.

In some circumstances, a tachycardia may be unresponsive to ATP therapies. In some of those circumstances, cardioversion may be indicated. Cardioversion therapies, like ATP therapies, may differ from one another and may be arranged in a hierarchy, with the first cardioversion therapy in the hierarchy applied first, the second cardioversion therapy in the hierarchy applied if the first fails, and so on. In general, cardioversion therapies may differ from one another by the amount of energy delivered during a cardioversion shock. In accordance with the invention, cardioversion therapies may also differ from one another by the synchronization delay.

A synchronization delay is a delay with respect to a cardiac event such as a detected P-wave, as reflected by a signal on P-out line 72, or a detected R-wave, as reflected by a signal on R-out line 76. The synchronization delay may be negligible, essentially zero. In other words, the cardioversion shock may be applied immediately upon detection of the cardiac event. The synchronization delay may cause the cardioversion shock to be applied at a time interval following detection of the cardiac event. Furthermore, the synchronization delay may be a "negative delay." Application of a negative delay causes the cardioversion shock to be applied before detection of an expected cardiac event. In practice, implementing a negative delay involves observing past cardiac events and predicting when a future cardiac event will occur.

When a cardioversion or defibrillation pulse is required, microprocessor 82 may control the timing, strength and duration of cardioversion and defibrillation pulses. In response to the detection of atrial or ventricular fibrillation or tachycardia requiring a cardioversion pulse, microprocessor 82 activates CV/defib control circuitry 64, which initiates charging of capacitor bank 68 via charging circuit 100, under the control of high voltage charging control line 102. The voltage on the high voltage capacitors is monitored via VCAP line 104, which is passed through multiplexer 86, and in response to reaching a predetermined value set by microprocessor 82, results in generation of a logic signal on Cap Full (CF) line 106 to terminate charging. A defibrillation or cardioversion pulse may be delivered by output circuit 62.

Figure 3:
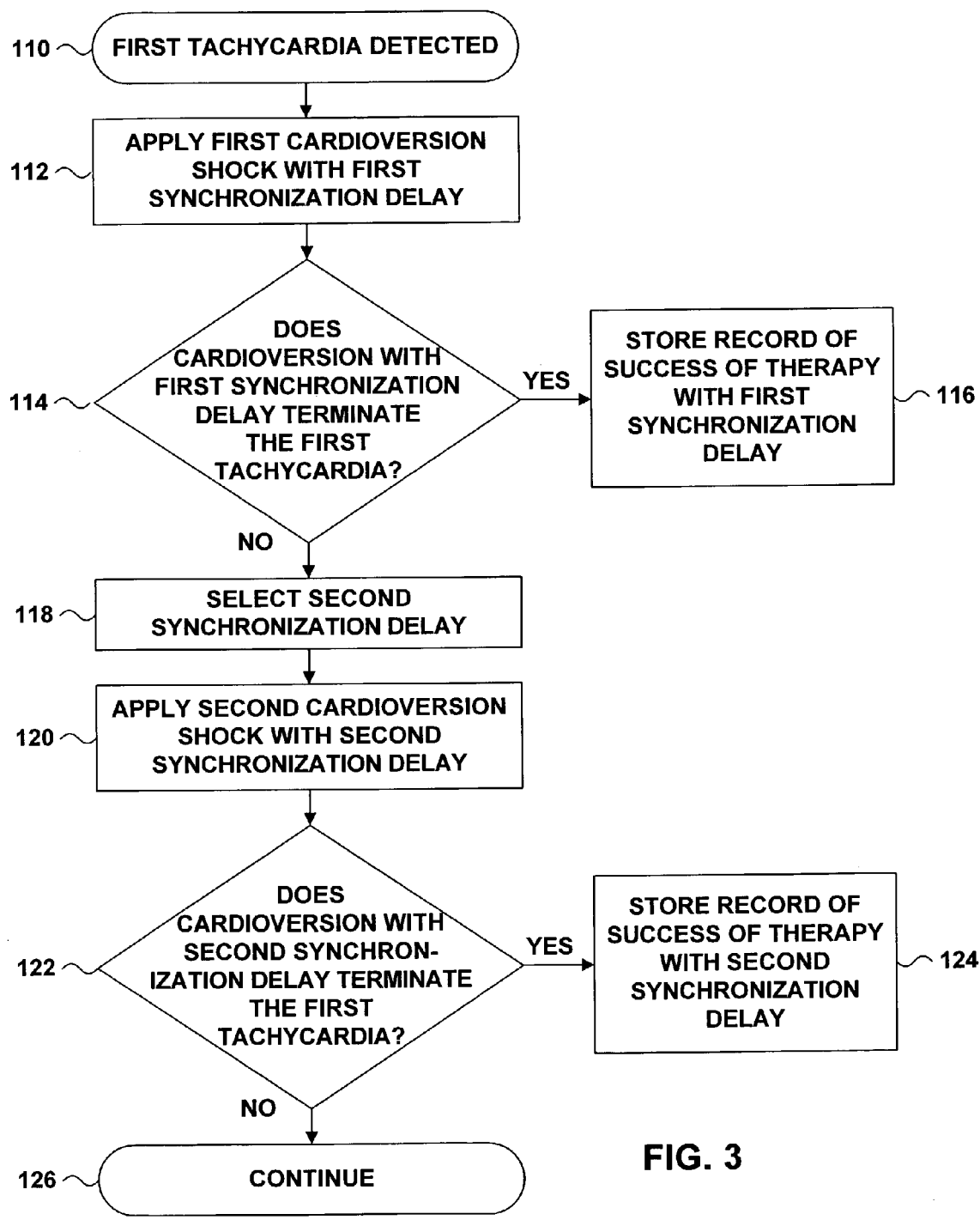
FIG. 3 is a flow diagram illustrating exemplary techniques for applying cardioversion shocks with synchronization delays.

FIG. 3 is a flow diagram illustrating techniques for adaptive timing of the delivery of cardioversion shocks. It is assumed that IMD 10 has detected a tachycardia (110) and that cardioversion is indicated. It is possible that other therapies have been applied prior to cardioversion, but the other therapies failed.

IMD 10 applies a first cardioversion shock to the heart with a first synchronization delay (112). The first synchronization delay is with respect to a first cardiac event. If the detected tachycardia is VT, for example, IMD 10 may apply the first cardioversion shock to the heart with respect to a first detected R-wave. The first synchronization delay may be negligible, or applied at an interval following the first cardiac event, or may be a negative delay.

IMD 10 monitors whether the first cardioversion shock terminates the tachycardia (114). If so, the IMD 10 may store a record of the success of the therapy in memory 90 (116). In some circumstances, however, the first cardioversion shock may fail to terminate the tachycardia, and a record of the failure may also be stored in memory 90. IMD 10 may apply additional cardioversion shocks like the first cardioversion shock, with the same or greater energy and the same first synchronization delay. If this cardioversion therapy fails, IMD 10 selects a second synchronization delay (118) and applies a second cardioversion shock with a second synchronization delay (120) with respect to a second cardiac event, e.g., a second detected R-wave.

The second synchronization delay may be an offset of the first synchronization delay. For example, the second synchronization delay may be approximately 100 milliseconds longer than the first synchronization delay. The second synchronization delay may also be selected from a set of possible synchronization delays. The selected second delay may be a negative delay.

IMD 10 monitors whether the second cardioversion shock terminates the tachycardia (122). If so, the IMD 10 stores a record of the success of the therapy in memory 90 (124). Should the second cardioversion shock, applied with the second synchronization delay, fail to terminate the tachycardia after repeated attempts, IMD 10 may continue applying therapies (126). Continuing applying therapies may include, for example, selecting a third synchronization delay and applying one or more cardioversion shocks with the third synchronization delay. Continuing applying therapies may also include applying cardioversion therapies at higher energy levels.

Figure 4:
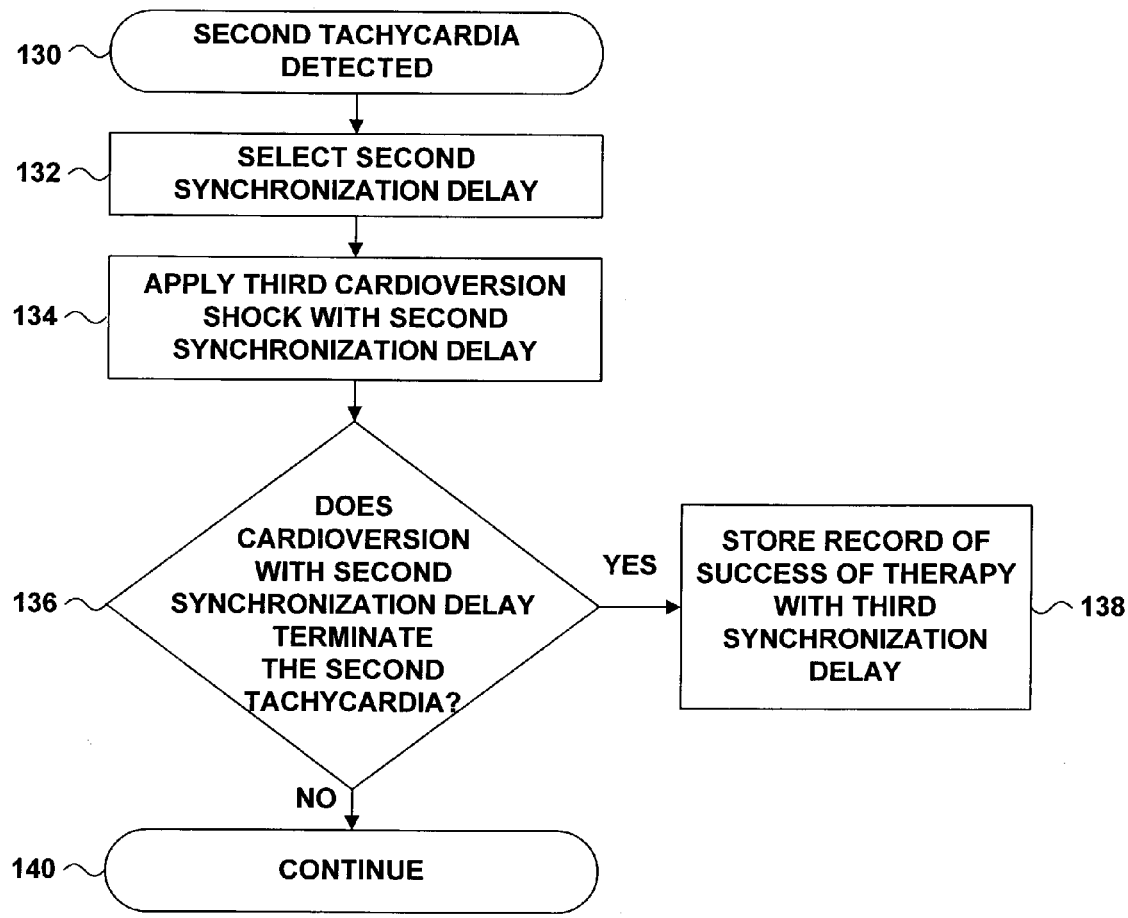
FIG. 4 is a flow diagram illustrating an exemplary technique for selecting a synchronization delay for a cardioversion shock.

FIG. 4 is a flow diagram that illustrates selection of a synchronization delay as a function of historical performance. For purposes of illustration, it is assumed that the first tachycardia depicted in FIG. 3 has been successfully terminated by cardioversion therapy applied with the second synchronization delay. It is further assumed that IMD 10 detects a second tachycardia (130) and that cardioversion is indicated once again.

IMD 10 selects a synchronization delay based upon past historical performance. In the past, the first cardioversion shock, applied with the first synchronization delay, failed to terminate the tachycardia. The second cardioversion shock, however, applied with the second synchronization delay, was successful in terminating the tachycardia. Accordingly, upon detection of the second tachycardia (130), IMD 10 selects the second synchronization delay (132) and IMD 10 applies a third cardioversion shock to the heart with the second synchronization delay (134). In other words, IMD 10 selects a synchronization delay that is historically effective. IMD 10 does not select the first synchronization delay, which was historically ineffective with a previous episode of tachycardia.

IMD 10 continues to monitor the performance of the cardioversion therapy, in particular, whether the third cardioversion shock terminates the tachycardia (136). If so, the IMD 10 may store a record of the success of the therapy in memory 90 (138). If not, IMD 10 may continue applying therapies (140) as described above.

After several tachycardia episodes, the records stored in memory may show that a first synchronization delay is the most effective synchronization delay employed so far, a second synchronization delay is the second most effective synchronization delay, and so on. Based upon these records, IMD 10 may generate a hierarchy of synchronization delays. When cardioversion therapy is applied, the most effective synchronization delay may be employed first, with the second most effective synchronization delay applied next, and so on. The historical performance of each synchronization delay may determine its position in the hierarchy. When IMD 10 detects subsequent episodes of tachycardia, IMD 10 may select a synchronization delay according to its position in the hierarchy, i.e., IMD 10 may select a synchronization delay as a function of historical performance.

IMD 10 may further monitor the effectiveness of cardioversion with each synchronization delay, and may omit a historically effective synchronization delay when that synchronization delay is no longer of benefit to the patient. A synchronization delay may be deemed no longer beneficial when application of a cardioversion shock with that synchronization delay fails to terminate one or more tachycardias, or when application of a cardioversion shock with that synchronization delay initiates fibrillation and makes the condition of the patient worse.

In addition to selecting synchronization delays, IMD 10 may select energy levels of cardioversion shocks by adjusting the amplitude of the shock or the pulse width, or both. In many forms of tachycardia, success of the cardioversion therapy is a function of the timing of the shock, not merely the quantity of energy delivered. It is possible that, with a well-timed cardioversion shock, a tachycardia may be terminated with a reduced quantity of energy. IMD 10 may therefore select a synchronization delay to conserve battery power.

The invention further reduces the number of cardioversion shocks applied to the patient. As IMD 10 acquires and stores more data pertaining to the effectiveness of cardioversion shocks with synchronization delays, episodes of tachycardia can be terminated more efficiently and with fewer shocks. Because cardioversion shocks are generally uncomfortable, fewer shocks means less patient discomfort.

Moreover, the adaptive timing of the delivery of cardioversion shocks is automatic, and requires no intervention by the patient or the physician for the patient.

A single medical device may apply different synchronization delays for AT and VT. In other words, the invention may be applied independently to AT and VT therapies.

In some medical devices, cardioversion and defibrillation functions overlap. As noted above in connection with FIG. 2, a device may use many of the same components when delivering the cardioversion and defibrillation shocks. Moreover, it may be difficult in some circumstances to distinguish a VF from a VT, because range of cycle lengths of VF may overlap the range of cycle lengths of VT.

Accordingly, a device that employs a synchronization delay with a cardioversion shock may employ a synchronization delay with a defibrillation shock as well. Fortunately, synchronization delays have an indifferent effect upon the efficacy of defibrillation shocks used to treat VF, but may have a favorable effect when a defibrillation shock is applied to a VT that resembles a VF. When a defibrillation shock is applied to a VT that resembles a VF, the defibrillation shock is, in effect, a cardioversion shock. Accordingly, synchronization delays may improve the efficacy of cardioversion therapies while doing no harm to defibrillation therapies.

The techniques of the invention also work in harmony with other therapies, such as ATP therapies. In a typical IMD, for example, adjustments to the timing of cardioversion shocks have no effect upon the timing of ATP paces.

The preceding specific embodiments are illustrative of the practice of the invention. Various modifications may be made without departing from the scope of the claims. For example, synchronization delays have been described with respect to cardiac events such as sensed P-waves and R-waves, but the invention is not limited to selecting synchronization delays with respect to these particular cardiac events. Embodiments of the invention can include cardiac paces, or P-waves and R-waves evoked in response to pacing, as cardiac events. Furthermore, the invention encompasses selecting a synchronization delays for ventricular cardioversion therapy with respect to a P-wave, and selecting a synchronization delays for atrial cardioversion therapy with respect to an R-wave.

Furthermore, as noted above, the invention is not limited to application in an implantable medical device. An external medical device such as an external defibrillator may practice the invention. In addition, the techniques described above may be embodied as a computer-readable medium comprising instructions for a programmable processor such as microprocessor 82 or pacer timing/control circuitry 94 shown in FIG. 2. The programmable processor may include one or more individual processors, which may act independently or in concert. A "computer-readable medium" includes but is not limited to read-only memory, Flash memory and a magnetic or optical storage medium. These and other embodiments are within the scope of the following claims.

What is claimed is:

1. A method comprising:
applying a first cardioversion shock to a heart experiencing a tachycardia, wherein the first cardioversion shock is applied with a first synchronization delay with respect to a first cardiac event;
monitoring whether the first cardioversion shock terminates the tachycardia; and
applying a second cardioversion shock to the heart when the first cardioversion shock fails to terminate the tachycardia, wherein the second cardioversion shock is applied with a second synchronization delay with respect to a second cardiac event,
wherein the first synchronization delay is negligible.

2. The method of claim 1, wherein the second synchronization delay is approximately 100 milliseconds longer than the first synchronization delay.

3. The method of claim 1, wherein the first cardiac event comprises a first detected R-wave and wherein the second cardiac event comprises a second detected R-wave.

4. A method comprising:
applying a first cardioversion shock to a heart experience a tachycardia, wherein the first cardioversion shock is applied with a first synchronization delay with respect to a first cardiac event;
monitoring whether the first cardioversion shock terminates the tachycardia; and
applying a second cardioversion shock to the heart when the first cardioversion shock fails to terminate the tachycardia, wherein the second cardioversion shock is applied with a second synchronization delay with respect to a second cardiac event,
wherein the second synchronization delay is a negative synchronization delay in which the second cardioversion shock precedes the second cardiac event.

5. The method of claim 4, further comprising:
monitoring whether the second cardioversion shock terminates the tachycardia; and
applying a third cardioversion shock to the heart when the second cardioversion shock fails to terminate the tachycardia, wherein the third cardioversion shock is applied with a third synchronization delay with respect to a third cardiac event.

6. The method of claim 1, wherein the tachycardia is a first tachycardia, the method further comprising:
monitoring whether the second cardioversion shock terminates the first tachycardia; and
applying a third cardioversion shock to the heart experiencing a second tachycardia, wherein the third cardioversion shock is applied with the second synchronization delay with respect to a third cardiac event.

7. The method of claim 1, wherein the tachycardia is a first tachycardia, the method further comprising:
monitoring whether the second cardioversion shock terminates the first tachycardia;
selecting a third synchronization delay as a function of whether the second cardioversion shock terminates the first tachycardia; and
applying a third cardioversion shock to the heart experiencing a second tachycardia, wherein the third cardioversion shock is applied with the third synchronization delay with respect to a third cardiac event.

8. A method comprising:
applying a first cardioversion shock to a heart experiencing a tachycardia, wherein the first cardioversion shock is applied with a first synchronization delay with respect to a first cardiac event;
monitoring whether the first cardioversion shock terminates the tachycardia;
applying a second cardioversion shock to the heart when the first cardioversion shock fails to terminate the tachycardia, wherein the second cardioversion shock is applied with a second synchronization delay with respect to a second cardiac event; and
further comprising applying a third cardioversion shock prior to the first cardioversion shock, wherein the third cardioversion shock is applied with the first synchronization delay with respect to a third cardiac event.

9. The method of claim 8, further comprising:
applying the first cardioversion shock at a first energy level; and
applying the second cardioversion shock at a second energy level.

10. The method of claim 9, wherein the second energy level is less than the first energy level.

11. The method of claim 8, further comprising storing in memory a record of whether the first cardioversion shock successfully terminates the tachycardia.

12. The method of claim 11, wherein the record is a first record, the method further comprising:
storing in memory a second record of whether the second cardioversion shock successfully terminates the tachycardia; and
generating a hierarchy of synchronization delays as a function of the first and second records.

13. A computer-readable medium comprising instructions for causing a programmable processor to:
apply a first cardioversion shock to a heart experiencing a tachycardia, wherein the first cardioversion shock is applied with a first synchronization delay with respect to a first cardiac event;
monitor whether the first cardioversion shock terminates the tachycardia; and
apply a second cardioversion shock to the heart when the first cardioversion shock fails to terminate to terminate the tachycardia, wherein the second cardioversion shock is applied with a second synchronization delay with respect to a second cardiac event,
wherein the first synchronization delay is negligible.

14. The medium of claim 13, wherein the second synchronization delay is approximately 100 milliseconds longer than the first synchronization delay.

15. The medium of claim 13, wherein the first cardiac event comprises a first detected R-wave and wherein the second cardiac event comprises a second detected R-wave.

16. A computer-readable medium comprising instructions for causing a programmable processor to:
apply a first cardioversion shock to a heart experiencing a tachycardia, wherein the first cardioversion shock is applied with a first synchronization delay with respect to a first cardiac event;
monitor whether the first cardioversion shock terminates the tachycardia; and
apply a second cardioversion shock to the heart when the first cardioversion shock fails to terminate the tachycardia, wherein the second cardioversion shock is applied with a second synchronization delay with respect to a second cardiac event,
wherein the second synchronization delay is a negative synchronization delay in which the second cardioversion shock precedes the second cardiac event.

17. The medium of claim 16, the instructions further causing the processor to:
monitor whether the second cardioversion shock terminates the tachycardia; and
apply a third cardioversion shock to the heart when the second cardioversion shock fails to terminate the tachycardia, wherein the third cardioversion shock is applied with a third synchronization delay with respect to a third cardiac event.

18. The medium of claim 16, wherein the tachycardia is a first tachycardia, the instructions further causing the processor to:
monitor whether the second cardioversion shock terminates the first tachycardia; and
apply a third cardioversion shock to the heart experiencing a second tachycardia, wherein the third cardioversion shock is applied with the second synchronization delay with respect to a third cardiac event.

19. The medium of claim 16, wherein the tachycardia is a first tachycardia, the instructions further causing the processor to:
monitor whether the second cardioversion shock terminates the first tachycardia;
select a third synchronization delay as a function of whether the first cardioversion shock terminates the first tachycardia and whether the second cardioversion shock terminates the first tachycardia; and
apply a third cardioversion shock to the heart experiencing a second tachycardia, wherein the third cardioversion shock is applied with the third synchronization delay with respect to a third cardiac event.

20. A computer-readable medium comprising instructions for causing a programmable processor to:
apply a first cardioversion shock to a heart experiencing a tachycardia, wherein the first cardioversion shock is applied with a first synchronization delay with respect to a first cardiac event;
monitor whether the first cardioversion shock terminates the tachycardia; and
apply a second cardioversion shock to the heart when the first cardioversion shock fails to terminate the tachycardia, wherein the second cardioversion shock is applied with a second synchronization delay with respect to a second cardiac event,
the instructions further causing the processor to apply a third cardioversion shock prior to the first cardioversion shock, wherein the third cardioversion shock is applied with the first synchronization delay with respect to a third cardiac event.

21. The medium of claim 20, wherein the first cardioversion shock is applied at a first energy level, and wherein the second cardioversion shock is applied at a second energy level.

22. The medium of claim 21, wherein the second energy level is less than the first energy level.

23. The medium of claim 20, the instructions further causing the processor to store in memory a record of whether the first cardioversion shock successfully terminates the tachycardia.

24. The medium of claim 23, wherein the record is a first record, the instructions further causing the processor to:
store in memory a second record of whether the second cardioversion shock successfully terminates the tachycardia; and
generate a hierarchy of synchronization delays as a function of the first and second records.

* * * * *

UNITED STATES PATENT AND TRADEMARK OFFICE
CERTIFICATE OF CORRECTION

PATENT NO.       : 7,181,273 B2
APPLICATION NO.  : 10/418853
DATED            : February 20, 2007
INVENTOR(S)      : Havel et al.

It is certified that error appears in the above-identified patent and that said Letters Patent is hereby corrected as shown below:

Column 10, line 11 please change "heart experience a" to --heart experiencing a--.

Signed and Sealed this

Twenty-third Day of October, 2007

JON W. DUDAS
*Director of the United States Patent and Trademark Office*